(12) United States Patent
Quaedflieg et al.

(10) Patent No.: US 8,883,444 B2
(45) Date of Patent: Nov. 11, 2014

(54) PEPTIDE SYNTHESIS USING ENZYMATIC ACTIVATION AND COUPLING

(75) Inventors: Peter Jan Leonard Mario Quaedflieg, Elsloo (NL); Timo Nuijens, Maastricht (NL); Claudia Cusan, Aachen (DE); Catharina Hubertina Maria Schepers, Stein (NL)

(73) Assignee: Enzypep B.V., Geleen (NL)

( * ) Notice: Subject to any disclaimer, the term of this patent is extended or adjusted under 35 U.S.C. 154(b) by 681 days.

(21) Appl. No.: 13/129,663

(22) PCT Filed: Nov. 19, 2009

(86) PCT No.: PCT/EP2009/065512
§ 371 (c)(1),
(2), (4) Date: Oct. 11, 2011

(87) PCT Pub. No.: WO2010/057961
PCT Pub. Date: May 27, 2010

(65) Prior Publication Data
US 2012/0129214 A1    May 24, 2012

(30) Foreign Application Priority Data
Nov. 19, 2008 (EP) .................................. 08169425

(51) Int. Cl.
*C12P 21/06* (2006.01)
*C07K 1/02* (2006.01)
*C12P 21/02* (2006.01)

(52) U.S. Cl.
CPC ............. *C12P 21/02* (2013.01); *C07K 1/026* (2013.01); *C07K 1/02* (2013.01)
USPC .......... 435/68.1; 435/219; 435/220; 435/221; 435/222; 435/196; 435/197; 435/198

(58) Field of Classification Search
USPC ........ 435/68.1, 219, 220, 221, 222, 196, 197, 435/198
See application file for complete search history.

(56) References Cited

FOREIGN PATENT DOCUMENTS

WO    WO 2007/045470        4/2007
WO    WO 2009047354 A1 *    4/2009

OTHER PUBLICATIONS

Miyazawa et al. J. Chem. Soc., Perkin Trans. (2001) 1:82-86.*
Miyazawa et al. Lett. Peptide Sci. (2003) 10: 83-87.*
Lin et al. Chemistry and Biology (2004) 11: 1635-1642.*
International Search Report for PCT/EP2009/065512, mailed Dec. 30, 2009.
Written Opinion of the International Searching Authority for PCT/EP2009/065512, mailed Dec. 30, 2009.
Miyazawa et al, "Broadening of the substrate tolerance of α-chymotrypsin by using the carbamoylmethyl ester as an acyl donor in kinetically controlled peptide synthesis" J. Chem Soc., Perkin Trans. 1, 2001, 87-93.

* cited by examiner

*Primary Examiner* — Susan Hanley
(74) *Attorney, Agent, or Firm* — Nixon & Vanderhye P.C.

(57) ABSTRACT

The invention relates to a method for synthesizing a peptide by enzymatically preparing an ester or thioester from (i) an N-terminal protected amino acid or an N-terminal protected peptide where either can have a protected C-terminal ester group and (ii) an alcohol represented by the formula HO—$CX_2$—Z or a thiol represented by the formula HS—$CX_2$—Z, each X independently representing a halogen atom or a hydrogen atom; and Z represents an electron withdrawing group comprising at least one $sp^3$-hybridized carbon comprising at least two substituents comprising a heteroatom directly attached to the at least one $sp^3$-hybridized carbon or at least one $sp^2$-hybridized carbon comprising one or two substituents comprising a heteroatom directly attached to the at least one $sp^2$-hybridized carbon, and enzymatically coupling the prepared ester or thioester with an optionally C-terminal protected amino acid or with an optionally C-terminal protected peptide in a medium comprising 2 wt. % water or less.

21 Claims, No Drawings

PEPTIDE SYNTHESIS USING ENZYMATIC ACTIVATION AND COUPLING

This application is the U.S. national phase of International Application No. PCT/EP2009/065512, filed 19 Nov. 2009, which designated the U.S. and claims priority to EP Application No. 08169425.9, filed 19 Nov. 2008, the entire contents of each of which are hereby incorporated by reference.

The invention relates to a method for enzymatically synthesising a peptide.

Peptides, in particular oligopeptides have many applications, for instance as pharmaceutical, food or feed ingredient, agrochemical or cosmetic ingredient.

For the purpose of this invention, with peptides is meant any chain of two or more amino acids. For the purpose of this invention, with 'oligopeptides' is meant a peptide based on 2-200 amino acids, in particular based on 2-100, more in particular based on 2-50 amino acids, preferably any linear chain of 2-200 amino acids, more preferably of 2-100 or 2-50 amino acids. The term 'polypeptides' is used for peptides based on a higher number of amino acids than specified for oligopeptides.

Chemo-enzymatic peptide synthesis, which is defined for the purpose of the invention as the synthesis of peptides in which one or more peptidic bonds are formed by an enzymatic coupling reaction, has several advantages over chemical peptide synthesis. For instance, the cost-price in case of large scale production is lower due to the fact that no or limited amino acid side chain protection is required. Also, the process is more environmentally friendly. For instance, no stoichiometric amounts of toxic chemical reagents, such as dicyclohexyl carbodiimide (DCC), 1-(3-dimethylaminopropyl)-3-ethylcarbodiimide hydrochloride (EDC) or 1-(3-dimethylaminopropyl)-3-ethylcarbodiimide methiodide (EDCI), are required. Further, such method may be carried out using less organic solvent. Furthermore, enzyme-catalyzed couplings are devoid of racemisation (see for instance Sewald and H.-D. Jakubke, in: "Peptides: Chemistry and Biology", $1^{st}$ reprint, Ed. Wiley-VCH Verlag GmbH, Weinheim 2002, p 250) leading to more pure products and/or easier isolation.

With respect to the chemo-enzymatic coupling method there are two options to generate the peptidic bond. In the so-called thermodynamic (or equilibrium-controlled) approach, the carboxy component, i.e. the component which is to be coupled on its C-terminus, bears a free carboxylic acid functionality, while in the kinetically controlled approach a reactive carboxy component is used, such as a primary n-alkyl ester.

The thermodynamic approach has three major disadvantages: i) the equilibrium is usually on the side of peptide bond cleavage so that the coupling yields are poor; ii) a large amount of enzyme is usually required; iii) the reaction rates are usually very low. In the kinetically controlled approach alkyl esters are required as starting material but much less enzyme is required, the reaction time is significantly shorter, and, above all, the maximum obtainable yields are usually considerably higher. Therefore, for industrial application, an enzymatic peptide synthesis concept based on a kinetic approach, i.e. using an activated carboxy component, is most attractive (see for instance N. Sewald and H.-D. Jakubke, in: "Peptides: Chemistry and Biology", 1st reprint, Ed. Wiley-VCH Verlag GmbH, Weinheim 2002, section 4.6.2).

Chemo-enzymatic peptide synthesis can be stepwise performed in the C→N terminal direction or in the N→C terminal direction but can also entail the enzymatic coupling of fragments which have individually been synthesized using chemical synthesis or by a combination of chemical and chemo-enzymatic coupling steps. Chen et al. describe the coupling in "low aqueous" organic solvents with a protease which is active and stable in the organic solvent (J. Org. Chem. 1992, 57, 6960-65, Biomed. Biochim. Acta 1991, 50, 181, Bioorg. Med. Chem. Lett. 1991, 1, 445). Disadvantages of the methods described therein are that only few enzymes are active and stable in low aqueous conditions and the enzymes have a limited substrate scope, in the methods as described in these publications. Therefore, long reaction times and a large excess of the amino acid or peptide nucleophile is usually required. Still there is sometimes some hydrolysis at other positions in the peptide and often transamidation occurs on existing peptidic bonds in one of the fragments (=enzyme-catalyzed nucleophilic attack of the amino acid or peptide nucleophile on one of the existing peptidic bonds). Hence, the yields are sometimes low. Further, the purification of the products is often difficult.

Another approach is the use of so-called "substrate mimetics", as reviewed by F. Bordusa et al in Current Protein and Peptide Science 2002, 3, 159-180. In this approach, the C-activated amino acid or peptide has an ester moiety which resembles a specific amino acid to such an extent that an enzyme which is selective for that specific amino acid rapidly reacts with any amino acid bearing the ester moiety. A good example is the use of 4-guanidinophenyl (Gp) esters as discovered by Bordusa et al. which resemble Arg to such an extent that trypsin, which is in its hydrolytic properties specific for Arg-X sequences (for which X stands for any proteinogenic amino acid), can couple almost any C-terminus (bearing a Gp ester) to various amino acid and peptide nucleophiles. For instance, N-protected D-Ala-OGp can be coupled to various amino acid and peptide nucleophiles as demonstrated by M. Thormann et al in Biochem. 1999, 38, 6056. Hence, also D-amino acids and non-proteinogenic amino acids can be incorporated enzymatically with high efficiency and, additionally, no hydrolysis of the peptidic bonds in the fragments occurs except if there is a peptidic bond for which the coupling enzyme is specific (e.g. Arg-X bonds in the case of trypsin). Disadvantages of the substrate mimetic approach are that substrate mimetics (such as Gp esters) require a laborious multi-step chemical synthesis which is difficult to scale up and by which often racemisation of the amino acid occurs; the substrate mimetics are also instable, and thus difficult to handle on a large scale and sometimes their solubility in aqueous solution is low.

In 'Organic Letters, 2001, Vol 3, No. 26, p 4157-4159' Liu and Tam report a method wherein subtilisin Carlsberg is used for catalysing the formation of C-terminal 3-hydroxypropyl or 4-hydroxybutyl esters of certain N-terminal Boc-protected amino acids and unprotected peptides in 1,3-propanediol and in 1,4-butanediol comprising 1-2.5% water. Further the enzymatic coupling of an amino acid (leucine) or a peptide to the obtained ester in a reaction medium (different from the medium wherein the ester formation has taken place) is described. The reaction medium wherein the coupling takes place comprises a substantial amount of water.

In 'Biotechnology and Bioengineering, 1997, vol. 54, no. 3, p 287-290' Mitin et al. report a method wherein papain is used for catalyzing the formation of C-terminal glyceryl esters of N-terminal Boc and N-terminal Cbz protected amino acids and peptides in glycerol containing at least 10 wt % of water giving the esters in maximally 70% yield. Use of solutions containing less than 10 wt % of water results in much lower ester yields due to denaturation of the papain.

Yet another approach is the use of "activated" esters such as carbamoylmethyl (Cam) esters (as described for instance by T. Miyazawa et al. J. Chem. Soc., Perkin Trans. 1, 2002, 390-395) or 2,2,2-trifluoroethyl esters (as described by A. Yan et al. Tetrahedron, 61, 2005, 5933-5941). These esters are usually more easily prepared and more stable than the "real" substrate mimetics but still need chemical steps that are expensive and environmentally unfriendly. Further, the preparation of these esters often leads to some racemisation of the amino acid. For instance Cam esters can be prepared by treatment of the Cs salts of the acyl donor with 2-chloroacetamide and Tfe esters can be prepared using carbodiimide chemistry. The Cam and Tfe esters are usually coupled to amino acid or peptide nucleophiles using cheap and readily available proteases such as papain and subtilisin. Hence, also D-amino acids can be incorporated into peptides (Pro has not been incorporated yet).

There remains a need for alternative methods for peptide synthesis and/or for preparing intermediate compounds that can be used for peptide synthesis, in general. Such methods may, e.g., provide additional methodology that increases flexibility in peptide synthesis and/or allow the synthesis of specific peptides that are not or relatively difficult to obtain using known methodology. For instance, it is still a challenge to enzymatically couple various amino acids in a good yield within an acceptable time. Therefore there is still a need for improved methodology for coupling not only proteinogenic but also non-proteinogenic amino acids, such as D-alpha-amino acids, beta-amino acids, phenylglycine, DOPA, alpha-alkylated amino acids, or a peptide of which the N-terminal amino acid residue is a residue of any of these amino acids, via their N-terminal amine function to the C-terminal carboxylic acid function of another amino acid or peptide. Further, there is still a need for improved technology for coupling not only proteinogenic but also non-proteinogenic amino acids such as D-alpha-amino acids, beta-amino acids, phenylglycine, DOPA, alpha-alkylated amino acids, or a peptide of which the C-terminal amino acid residue is a residue of any of these amino acids, via their C-terminal carboxyl function to the N-terminal amine function of another amino acid or peptide.

Further, there is in particular a need for improved technology with respect to enzymatically coupling any amino acid or peptide via its N-terminal amine function to the C-terminal carboxylic acid function of a sterically hindered amino acid, such as valine or isoleucine, or a peptide of which the C-terminal amino acid residue is a sterically hindered amino acid, such as valine or isoleucine.

Further, there remains a need for new relatively simple methods that are relatively environmentally friendly.

It has now been found possible to provide such methodology by combining the enzymatic preparation of an activated C-terminal ester or of an activated C-terminal thioester of an amino acid or peptide and enzymatically coupling this activated ester or activated thioester with another amino acid or peptide in a specific way.

Accordingly, the present invention relates to a method for enzymatically synthesising a peptide, comprising enzymatically preparing an ester or a thioester from (i) an N-terminal protected amino acid, an N-terminal protected amino acid C-terminal ester, an N-terminal protected peptide, or an N-terminal protected peptide C-terminal ester and (ii) an alcohol represented by the formula HO—$CX_2$—Z respectively a thiol represented by the formula HS—$CX_2$—Z each X independently representing a halogen atom or a hydrogen atom; and Z being selected from the group of $sp^3$-hybridised carbons comprising at least two substituents comprising a heteroatom directly attached to the $sp^3$-hybridised carbon and $sp^2$-hybridised carbons comprising one or two substituents comprising a heteroatom directly attached to the $sp^2$-hybridised carbon, The preparation of the ester or thioester being carried out in a reaction medium comprising 2 wt. % water or less based on the weight of liquids in the reaction medium; and Enzymatically coupling the prepared ester or thioester with an, optionally C-terminal protected, amino acid or with an, optionally C-terminal protected, peptide, thereby synthesising the peptide in a reaction medium comprising 2 wt. % water or less based on the total weight of the reaction medium.

The term 'C-terminal protected' is used herein to indicate that a C-terminal carboxyl-group is provided with a protective group, generally substantially protecting the carboxyl group from being coupled to an amine group of another molecule. In particular, the C-terminal protective group may be a C-terminal ester whereby the C-terminal carboxyl group is at least substantially protected from being coupled to an amine under peptide synthesis conditions used. A t-alkyl group is a commonly used protective group.

The term 'N-terminal protected' is used herein to indicate that an N-terminal amine group is provided with a protective group, generally at least substantially protecting the N-terminal amine group from participating in coupling of a C-terminal carboxyl group to the N-terminal amine group.

The ester or thioester prepared in a method of the invention may respectively be referred to as an 'activated ester' or an 'activated thioester', as such ester is capable of participating in the coupling reaction. In contrast, the free C-terminal carboxylic acid or the ester which may be used for the preparation of the activated ester, is not capable to participate in the coupling, or at least has a substantially lower reactivity in the coupling reaction, e.g. less than half of the reactivity, less than one tenth of the reactivity or less than one hundredth of the reactivity of the activated ester that is enzymatically prepared in the method of the invention. In particular, for amino acids, C-terminal amino acid residues or N-terminal amino acid residues that are conventionally difficult to couple (having a low coupling rate), a large increase in coupling rate can be achieved by a method of the invention due to activation of the amino acid or C-terminal amino acid residue. Typical examples of difficult to couple amino acids or amino acid residues are D-amino acids or amino acid residues thereof and other non-proteinogenic amino acids or amino acid residues thereof. Further examples include sterically hindered amino acids, e.g. valine and isoleucine, or amino acid residues thereof.

The enzymatic preparation of the ester or thioester, respectively, may be referred to hereinafter as an esterification or thioesterification, respectively. This term includes the case wherein the preparation of the (thio)ester involves the reaction of an N-terminal protected amino acid or peptide C-terminal ester with the (thio)alcohol. More specifically such reaction is known as a trans(thio)esterification.

In an embodiment, the method of the invention is advantageous in that it offers the possibility to use a method of the invention for the coupling of various amino acids or various peptides differing in the terminal amino acid residue that is to participate in the coupling reaction, including proline and non-proteinogenic amino acids or peptides containing proline or a non-proteinogenic terminal amino acid residue to take part in the coupling.

In an embodiment, the method of the invention is advantageous in that the activated (thio)esters are synthesized in high yields without racemisation or other side reactions in an environmentally friendly way, i.e. not producing stoichiometric amounts of waste compounds.

In an embodiment, the method of the invention is advantageous in that it offers a high stability and/or activity of the enzyme or enzymes used in the method.

In an embodiment, the method of the invention is advantageous in that the extent of hydrolysis of the enzymatically prepared ester is small (within a typical time frame for achieving the preparation of the (thio)ester and the coupling), at least in several embodiments no detectable hydrolysis of the ester has been observed.

In an embodiment, the method of the invention is advantageous in that the extent of hydrolysis of the enzymatically prepared peptide is low; at least in several embodiments no detectable hydrolysis of the enzymatically prepared peptide has been observed.

In an embodiment, the method of the invention is advantageous in that it offers a high overall reaction rate, i.e. a high conversion rate from the N-protected amino acid or peptide starting compounds to synthesised peptides, leading to relatively short reaction times to achieve a specific yield.

In particular, a method of the invention allows coupling of an amino acid or peptide to another amino acid or peptide, without needing a large excess of one of the coupling partners in order to obtain the synthesised peptide in an acceptable yield based on the other coupling partner within a relatively short time. The molar ratio of the N-terminal protected amino acid, the N-terminal protected amino acid C-terminal ester, the N-terminal protected peptide, or the N-terminal protected peptide C-terminal ester from which the (activated) (thio)ester is prepared to the optionally C-terminal protected amino acid or peptide usually is chosen in the range of 2:1 to 1:3, in particular in the range of 1:1 to 1:2, preferably in the range of 1:1 to 1:1.5. In a specifically preferred method, said molar ration is in the range of 1:1 to 1:1.1.

A method of the invention is in particular advantageous in that it has been found possible to enzymatically prepare activated C-terminal esters or thioesters of an N-terminal protected amino acid or an N-terminal protected peptide, in particular C-terminal carbamoylmethyl (Cam) esters or C-terminal 2,2,2-trifluoroethyl (Tfe) esters of an N-terminal protected amino acid or an N-terminal protected peptide, as part of a chemo-enzymatic peptide synthesis. In particular, it has surprisingly been found that Cam and Tfe esters can be prepared enzymatically in a high yield using a protease or a lipase, and, even better, that the activation step with the protease or lipase can be performed simultaneously with the peptidic bond formation step using a protease giving the condensation product (the peptide to be synthesised) without noticeable side reactions in a yield of more than 90%, even when using equimolar amounts of the amino acids or peptides to be coupled, i.e. without needing an excess of the amino acid or peptide acting as the nucleophile.

Further, it has been found that it is possible to synthesise peptides without noticeable racemisation, also in case a "difficult" amino acid, such as Proline, or a non-proteinogenic amino acid, e.g. a D-amino acid, is present on one or both sides of the peptidic bond to be assembled.

A method according to the invention in particular offers a relatively simple process because it is possible to carry out (thio)esterification in a so-called 'one-pot' process. In a one-pot process (thio)esterification and coupling take place without carrying out an isolation step (of the prepared ester or thioester) in between these reactions. It is even possible to carry out a method according to the invention by including all substances (such as amino acid(s) or ester(s) thereof and/or peptide(s) or ester(s) thereof to be coupled, alcohol/thiol, solvent and enzyme(s)) from the start of the reaction, which may be particularly beneficial with respect to obtaining the peptide to be synthesised with a high yield in a relatively short time. Accordingly, in a particularly suitable one-pot method of the invention, the preparation of the ester or thioester is carried out in the presence of optionally C-terminal protected amino acid or optionally C-terminal protected peptide with which the ester or thioester that is prepared is to be coupled.

In a further one-pot method of the invention the (thio)esterification and coupling take place sequentially, i.e. the optionally C-terminal protected amino acid or the optionally C-terminal protected peptide is added after the ester or thioester has been prepared.

In a further one-pot method of the invention, first the preparation of the (thio)ester is carried out using a lipase or esterase, and thereafter an enzyme is added (usually a protease) for catalysing the coupling reaction. Such approach may in particular be followed in case the enzyme catalysing the coupling is detrimental to the preparation of the (thio)ester, e.g. because it has an adverse effect on the activity or stability of the enzyme catalysing the preparation of the (thio)ester.

It is also possible to use an intermediate form of these one-pot methods, such as initially including only part of one or more of the substances used in the method of the invention, and add the remainder later. In particular, part of optionally C-terminal protected amino acid or optionally C-terminal protected peptide with which the ester or thioester that is prepared is to be coupled may be added gradually or stepwise.

In principle, the enzyme catalysing the (thio)esterification and the enzyme catalysing the coupling may be the same, in particular the same lipase, esterase, or protease. For instance, subtilisin Carlsberg or *Candida antarctica* lipase B may be used for such an embodiment.

It has been found particularly advantageous with respect to obtaining the synthesised peptide within a relatively short time to use at least two enzymes, namely at least one enzyme selected from the group of lipases and esterases and at least one protease. It is contemplated that in a one-pot method of the invention the lipase or esterase (primarily) catalyses the (thio)esterification and the protease (primarily) catalyses the coupling reaction.

The N-terminal protected amino acid or N-terminal protected peptide that is to be (thio)esterified may in principle be any amino acid, proteinogenic or non-proteinogenic or any peptide, based on proteinogenic and/or non-proteinogenic amino acids.

In a preferred embodiment, the invention relates to a method according to the invention, wherein for the enzymatic preparation of the ester or thioester (i) an N-terminal protected amino acid or an N-terminal protected peptide is reacted with (ii) the alcohol represented by the formula HO—CX$_2$—Z, respectively the thiol represented by the formula HS—CX$_2$—Z.

In particular, the N-terminal protected amino acid or peptide may be represented by a compound of formula I.

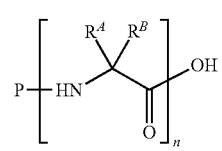

I

Herein P stands for an N-terminal protecting group. Suitable N-terminal protecting groups are those N-protecting groups which can be used for the synthesis of (oligo)peptides.

Such groups are known to the person skilled in the art. Examples of suitable N-protecting groups include carbonyl type protective groups, for instance 'Cbz' (i.e. benzyloxycarbonyl), 'Boc' (i.e. t-butyloxycarbonyl), 'For' (i.e. formyl), Fmoc (i.e. 9-fluorenylmethoxycarbonyl) and 'PhAc' (i.e. phenacetyl). The groups For or PhAc may be introduced and cleaved enzymatically using the enzymes Peptide Deformylase or PenG acylase, respectively. Chemical cleavage methods are generally known in the art.

Herein, n is an integer of at least 1. n may in particular be at least 2, at least 3, at least 4, at least 5, at least 6, at least 8, at least 9 or at least 10. n may in particular be 100 or less, 75 or less, 50 or less, 25 or less, 20 or less 15 or less or 10 or less, e.g. 5 or less.

Each $R^A$ and each $R^B$ independently represent H, or an organic moiety, preferably an amino acid side chain. Thus, it is not required that $R^A$ is the same in all n amino acid units. Similarly, it is not required that $R^B$ is the same in all n amino acid units.

In the context of the invention with 'amino acid side chain' is meant any proteinogenic or non-proteinogenic amino acid side chain. The reactive groups in the amino acid side chains may be protected by amino acid side chain protecting groups or may be unprotected. Suitable protecting groups for the side chains of the amino acids are known to a man skilled in the art. In particular, all or a part of the acidic or alkaline side groups may be provided with a protective group in order to improve the solubility of the amino acid or peptide, if desired.

Proteinogenic amino acids are the amino acids that are encoded by the genetic code. Proteinogenic amino acids include: alanine, valine, leucine, isoleucine, serine, threonine, methionine, cysteine, asparagine, glutamine, tyrosine, tryptophan, glycine, aspartic acid, glutamic acid, histidine, lysine, arginine, proline and phenylalanine.

Non-proteinogenic amino acids may in particular be selected amongst D-amino acids, phenylglycine, DOPA (3,4-dihydroxy-L-phenylalanine), beta-amino acids, 4-fluorophenylalanine, or alfa-alkylated amino acids.

In a specific embodiment, the N-terminal protected amino acid or peptide used for the preparation of the ester or thioester that is to take part in the coupling reaction is a C-terminal ester different from the (thio)ester that is to be prepared, for instance a t-alkyl ester or another ester which generally does not show substantial activity in an enzymatic coupling reaction for the synthesis of peptides, or at least a lower activity than the (thio)ester that is prepared. In such case, the preparation of the (thio)ester may be referred to as a trans(thio)esterification.

In an embodiment wherein the compound that is to be reacted with an alcohol or thiol that is to be prepared is an ester, it is typically an ester of an amino acid or peptide as described above.

Thus, the ester may be represented by the formula II

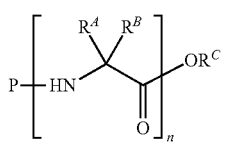

This ester typically is less reactive in the coupling reaction than the ester or thioester that is enzymatically prepared in the method of the invention. In general, this means that the $R^C$ group is not an electron withdrawing group, or is less electron withdrawing than the $CX_2$—Z group of the alcohol or thiol used in the preparation of the ester or thioester. $R^C$ usually is a hydrocarbon group or a hydrocarbon group comprising a substituent at a carbon in the gamma position relative to the ester or more remote from the ester moiety. In particular $R^C$ may be an alkyl group, in particular a C1-C6 alkyl group, more in particular a methyl group, an ethyl group, a primary propyl group, a secondary propyl group, a primary butyl group, a secondary butyl group, or a tertiary butyl group.

P, $R^A$, $R^B$, and n are as identified above.

The alcohol HO—$X_2$—Z or thiol HS—$X_2$—Z used in the preparation of the (thio)ester generally is an activating alcohol or thiol. An activating alcohol or thiol is an alcohol or thiol which provides an activated C-terminal carboxy (thio)ester group after (thio)esterification, i.e. a carboxy (thio)ester group that can take part in the coupling reaction. As indicated above, the alcohol is represented by the formula HO—$CX_2$—Z, or the thiol is represented by the formula HS—$CX_2$—Z.

Herein, each X independently represents a halogen atom (F, Cl, Br, I) or a hydrogen atom. In case an X is a halogen atom, it is preferably F. Good results have been achieved in a method of the invention wherein both X's are hydrogen.

Usually Z represents an electron withdrawing group. Without being bound by theory it is believed that this is advantageous with respect to the coupling reaction rate.

Z represents an $sp^2$ or $sp^3$ hybridised carbon atom comprising one or more substituents comprising a heteroatom. It is in general difficult or at least laborious to chemically prepare C-terminal (thio)esters of N-terminal protected amino acids or N-terminal protected peptides and such an alcohol or thiol. Thus, the present invention is further in particular advantageous in that a relatively simple method is provided for preparing such esters.

In a specific embodiment, Z is selected from the group of $sp^3$-hybridised carbons comprising one substituent comprising a heteroatom, which heteroatom is directly bound to the $sp^3$-hybridised carbon.

In a preferred embodiment, Z is selected from the group of $sp^3$-hybridised carbons comprising two or three substituents comprising a heteroatom, wherein said heteroatom of each of the substituents is directly bound to the $sp^3$-hybridised carbon, in particular two or three halogen substituents, preferably two or three halogen substituents selected from the group of F and Cl, e.g. Z may represent a trifluoromethyl group or a trichloromethyl group. Good results have for instance been achieved with 2,2,2-trifluorethyl alcohol (X=H, Z=$CF_3$), especially in a method wherein use is made of both a lipase and a protease. It is particularly surprising that an N-terminal protected amino acid trifluoroethylester or an N-terminal protected peptide C-terminal 2,2,2-trifluoroethylester can be prepared enzymatically from an N-terminal protected amino acid or peptide and subsequently be used in an enzymatic coupling method, and even more that it is possible to accomplish this in a one-pot process with a good yield.

In a further preferred embodiment, Z is selected from the group of $sp^2$-hybridised carbons comprising at least one substituent comprising a heteroatom, which heteroatom is directly bound to the $sp^2$-hybridised carbon. In particular, such Z may be a —(C=O)$R^1$ or a —(C=S)$R^1$. $R^1$ may in particular be selected from the group of amine groups, such as —$NH_2$, $NHCH_3$ or $N(CH_3)_2$, (optionally) C-terminal protected alpha-amino acids or (optionally) C-terminal protected peptides, preferably —$NH_2$; —OH or a salt thereof such as an alkali or ammonium salt; alkyl or aryl groups; substituted alkyl or aryl groups, in particular substituted alkyl or aryl groups comprising one or more halogen substituents; —$OR^2$; —$SR^2$. The $R^2$ group usually is a hydrocarbon or a substituted hydrocarbon, in particular an alkyl, a substituted alkyl (such as an alkyl comprising one or more halogen substituents) an unsubstituted aryl group or a substituted aryl group (such as an aryl comprising one or more halogen substituents). The alkyl or substituted alkyl in $R^1$ or $R^2$ may in particular comprise 1-6 carbon atoms; the unsubstituted or substituted aryl group may in particular comprise 5-18 carbon atoms in the ring or rings, more in particular 6-12.

Good results have for instance been achieved with carbamoylmethyl alcohol (Z=—(C=O)NH$_2$, carbamoyl), especially in a method wherein use is made of both a lipase and a protease. It is particularly surprising that an N-terminal protected amino acid C-terminal carbamoylmethylester or N-terminal protected peptide C-terminal carbamoylmethylester can be prepared enzymatically from an N-terminal protected amino acid or an N-terminal protected peptide and subsequently be used in an enzymatic coupling method, and even more that it is possible to accomplish this in a one-pot process with a good yield.

The optionally C-terminal protected amino acid or optionally C-terminal protected peptide that is to be coupled with the (thio)ester may in principle be any amino acid, proteinogenic or non-proteinogenic, or any peptide, based on proteinogenic and/or non-proteinogenic amino acids.

In particular, the optionally C-terminal protected amino acid or peptide may be represented by a compound of formula III:

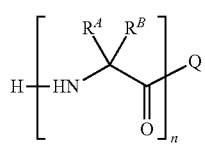

III

Herein, n, each $R^A$ and each $R^B$ are as defined above.

Herein Q represents an amide group or an OR moiety (see below).

In case Q represents an amide group, the amide group may be represented by the formula NR$_1$R$_2$ in which R$_1$ and R$_2$ may each individually represent any (substituted) alkyl or (substituted) aryl group. In particular, one out of R$_1$ and R$_2$ is a H atom and the other a (substituted) alkyl group. Preferably R$_1$ and R$_2$ are both H.

In case Q represents an OR moiety, R may represent a C-terminal protective group or a cation, for instance a monovalent cation, such as a tri- or tetrasubstituted ammonium ion or an alkaline metal cation or a H. In case R is a C-terminal protective group this may in particular be an optionally substituted alkyl group. Preferably it is a t-alkyl group, although in principle it also may be any other protective ester as known to a man skilled in the art. The t-alkyl may in principle be any protective tertiary alkyl group. Preferably the t-alkyl is selected from the group of t-butyl (2-methyl-2-propyl), t-pentyl (2-methyl-2-butyl) and t-hexyl (2,3-dimethyl-2-butyl). Good results have in particular been achieved with t-butyl. Usually, in order to avoid undesired side-reactions it is preferred that Q represents an amide group or an OR moiety in which R is a protective group. However, at least in some embodiments such side-reactions are adequately avoided otherwise.

As indicated above, in a method of the invention the (thio) esterification of the amino acid or peptide is catalysed by an enzyme, as is the coupling of the resultant (thio)ester to another peptide or amino acid. In principle any enzyme known in the art capable of catalyzing one or both of these reactions can be used. When referring to an enzyme from a particular source, recombinant enzymes originating from a first organism, but actually produced in a (genetically modified) second organism, are specifically meant to be included as enzymes from that first organism.

Examples of organisms from which an enzyme used in a method of the invention may be derived include *Trichoderma* species, such as from *Trichoderma reesei*; *Rhizopus* species, such as from *Rhizopus oryzae*; *Bacillus* species, such as from *Bacillus licheniformis, Bacillus subtilis Bacillus amyloliquefaciens, Bacillus clausii, Bacillus lentus, Bacillus alkalophilus, Bacillus halodurans*; *Aspergillus* species, such as from *Aspergillus oryzae* or *Aspergillus niger*; *Streptomyces* species, such as from *Streptomyces caespitosus* or *Streptomyces griseus*; *Candida* species; fungi; *Humicola* species; *Rhizoctonia* species; *Cytophagia*; *Mucor* species; and animal tissue, in particular from pancreas, such as from porcine pancreas, bovine pancreas or sheep pancreas.

It will be clear to the average person skilled in the art that use can also be made of mutants of naturally occurring (wild type) enzymes in a method according to the invention. Mutants of wild-type enzymes can for example be made by modifying the DNA encoding the wild-type enzymes using mutagenesis techniques known to the person skilled in the art (random mutagenesis, site-directed mutagenesis, directed evolution, gene shuffling, etc.) so that the DNA encodes an enzyme that differs by at least one amino acid from the wild-type enzyme or so that it encodes an enzyme that is shorter compared to the wild-type and by effecting the expression of the thus modified DNA in a suitable (host) cell. Mutants of the enzyme may have improved properties, for instance with respect to one or more of the following aspects: substrate scope, activity, stability, organic solvent resistance, temperature profile, synthesis/hydrolysis ratio and side reaction profile.

In a preferred method a lipase and/or a protease are used to catalyse at least one of said reactions.

A suitable lipase or esterase is selected from enzymes classifiable under EC 3.1. In particular a carboxylic ester hydrolase (E.C. 3.1.1) or a thiolester hydrolase (E.C. 3.1.2) may be used. In a preferred method a lipase is used selected from the group of lipases from *Candida*. Good results, in particular with respect to catalysing the (thio)esterification, have been achieved with *Candida antarctica* lipase, in particular with *Candida antarctica* lipase B.

A suitable protease is selected from enzymes classifiable under EC 3.4. Proteases can be further divided into two subclasses, the exopeptidases, acting only near the terminus of a peptide, and the endopeptidases that act internally in a peptide.

In an embodiment of the present invention, the enzymatic preparation of the ester or thioester is catalysed by a lipase or an esterase; and the enzymatic coupling is catalysed by a protease.

The exopeptidases acting at the N-terminus of a peptide release a single amino acid (aminopeptidases E.C. 3.4.11) or dipeptides (dipeptidases, E.C. 3.4.13) or both dipeptides and tripeptides (dipeptidyl-peptidases or tripeptidyl-peptidases, E.C. 3.4.14). The peptidases acting at the C-terminus of a peptide are called carboxypeptidases and liberate a single amino acid (carboxypeptidases, E.C. 3.4.16-18) or a dipeptide (peptidyl-dipeptidases, E.C. 3.4.15). The carboxypeptidases are grouped according to their catalytic mechanism, e.g. serine-type carboxypeptidases (E.C. 3.4.16), metallocarboxypeptidases (E.C. 3.4.17), cysteine-type carboxypeptidases (E.C. 3.4.18) or cleave terminal amino acids that are substituted, cyclised, or that have isopeptide bonds (peptide bonds involving the side chain) (omega-peptidases, E.C. 3.4.19).

In particular an endopeptidase may be used, especially an endopeptidase selected from the group of serine endopeptidases (E.C. 3.4.21), cysteine endopeptidases (E.C. 3.4.22), aspartic endopeptidases (E.C. 3.4.23) and metalloendopeptidases (E.C. 3.4.24).

Particularly suitable is a serine endopeptidase selected from the group of subtilisins. Such enzyme has been found particularly suitable for catalysing the coupling.

Various subtilisins are known in the art, see e.g. U.S. Pat. No. 5,316,935 and the references cited therein.

Subtilisin A is a commercially available subtilisin from Novozymes.

Particularly preferred is subtilisin Carlsberg, which when used in combination with a lipase, such as *Candida antarctica* lipase, has been found particularly advantageous with respect to synthesising a peptide with good yield in a relatively short time.

Alcalase® is a suitable source for subtilisin Carlsberg. This product is available from Novozymes (Bagsvaerd, Denmark). Alcalase® is a cheap and industrially available proteolytic enzyme mixture produced by *Bacillus licheniformis* (containing subtilisin Carlsberg as a major enzyme component).

Commercially available enzyme, such as Alcalase®, may be provided by the supplier as a liquid, in particular an aqueous liquid. In such case, the enzyme is preferably first isolated from undesired liquid, for instance excess water, or alcohols that cause an undesired side-reaction. This may suitably be accomplished by precipitating, usually followed by separation of the solid from the liquid, and/or drying. Precipitation may be accomplished using the alcohol, such as t-butanol, or an alcohol or thiol used in the method of the invention. In case another alcohol or thiol is used, care should be taken that such alcohol or thiol does not interfere adversely with the (thio) esterification reaction or the coupling reaction.

In a preferred embodiment, at least one of the enzymes is immobilised on a solid support. At least in some embodiments this may result in an increased yield of synthesised peptide after a relatively short reaction time, in particular in a one-pot process wherein both an enzyme for the catalysis of the (thio)esterification and a different enzyme for the catalysis of the coupling are used. Herein it is particularly preferred to use at least an immobilised enzyme for catalysing the (thio)esterification, in particular in case a lipase, such as *Candida antarctica* lipase, and a protease, such as subtilisin Carlsberg, are used. Particularly good results have been obtained with Alcalase cross-linked enzyme aggregates (Alcalase-CLEAs) wherein the Alcalase has been immobilized by condensation with glutaraldehyde.

In a specific embodiment at least two different enzymes are used, at least one catalysing the preparation of the (thio)ester and at least one other catalysing the coupling, wherein the different enzymes are immobilised on the same support.

It is possible to carry out the reaction in a mixture comprising the alcohol for the (thio)esterification and optionally an inert organic solvent, for instance acetonitrile, a hydrocarbon, such as toluene, or an ether, such as methyl-t-butyl ether (MTBE).

It is an advantage of the invention that it is not necessary to have thiol or alcohol used for the preparation of the (thio)ester present in large excess with respect to the amino acid or peptide that is to be esterified. For instance the molar ratio of said thiol or alcohol to said amino acid or peptide can be 50:1 or less, preferably 25:1 or less, in particular 20:1 or less, more in particular 10:1 or less. Usually, the ratio is at least 1:1. Preferably said molar ratio is at least 3:1, in particular at least 5:1, in order to allow the (thio)esterification to proceed at an advantageous rate.

A method of the invention is carried out under substantially non-aqueous conditions. As the skilled person will understand, a small amount of water may be desired, depending upon the enzyme(s), to enable the enzyme(s) to properly perform a desired catalytic activity. For a good catalytic activity the presence of a trace of water, e.g. of at least 0.005 wt. %, based on the liquid phase, may be desired. In particular, the water concentration may be at least 0.01 wt. % or at least 0.03 wt. %.

A desired upper limit for the water concentration depends on the specific enzyme(s), the alcohol or thiol used, the nature of the peptide to be synthesised (e.g. size, the amino acids upon which the peptide is based), the desired final conversion and the desired reaction rate.

The reaction medium usually contains, at least at the beginning of the activation or (trans)esterification less than 2.0 wt. % water, based on the weight of liquids in the reaction medium. The reaction medium may be dispersed in a second liquid phase or another liquid phase may be dispersed in the reaction medium. In case of a dual or multiphase system, the specified water content is based on the weight of liquid in the phase wherein the (trans)esterification or activation reaction—at least predominantly—takes place.

In particular, the water concentration may be less than 1.0 wt. % or less, at least at the beginning of the (thio)esterification. Advantageously, the method may be carried out in a medium containing 0.5 wt. % or less water, in particular 0.2 wt. % or less water, more in particular 0.1 wt. % or less water, at least at the beginning of the reaction, whilst still retaining substantial desired enzyme activity and a low, or even undetectable, undesired hydrolysis. In fact, at least in some embodiments, notably in an embodiment where *Candida antarctica* lipase and/or subtilisin Carlsberg are used, an improved peptide synthesis rate has been observed in a reaction medium having a very low water content, in particular in a reaction medium having a water content of less than 0.5 wt. % or less than 0.1 wt. %, compared to a method carried out in a reaction medium comprising 1-2.5% water.

In an advantageous method, water that is formed, in particular during (thio)esterification, may be removed continuously or intermittently. In principle removal may be accomplished in a manner known in the art. Good results have in particular been achieved using molecular sieves. Also very suitable for the removal is evaporation, such as azeotropic removal using vacuum or distillation.

In principle the pH used (in as far as a pH exists in the chosen reaction medium) may be chosen within wide limits, as long as a pH is chosen at which the enzyme shows sufficient activity. Such a pH is usually known for the enzyme to be used and may be based on its known hydrolytic activity in an aqueous solution, or can be routinely determined, making use of a known substrate for the enzyme under known reaction conditions. It may in particular be chosen to be about neutral. If desired, alkaline or acidic conditions may be used, depending on the enzyme. If desired, the pH may be adjusted using an acid and/or a base or buffered with a suitable combination of an acid and a base. Suitable acids and bases are in particular those soluble in the reaction medium, e.g. from the group of ammonia and alcohol-soluble acids, e.g. acetic acid and formic acid.

In principle the temperature used is not critical, as long as a temperature is chosen at which the enzyme(s) used show sufficient activity and stability. Such a temperature is usually known for the enzyme(s) to be used or can be routinely determined, making use of a known substrate for the enzyme(s) under known reaction conditions. Generally, the temperature may be at least 0° C., in particular at least 15° C. or at least 25° C. In particular if one or more enzyme(s) originating from a thermophilic organism are used, the temperature may preferably be at least 40° C. A desired maximum temperature depends upon the enzyme(s). In general such maximum temperature is known in the art, e.g. indicated in a product data sheet in case of commercially available enzyme(s), or can be determined routinely based on common general knowledge and the information disclosed herein. The temperature is usually 70° C. or less, in particular 60° C. or less or 45° C. or less. However, in particular if one or more enzyme(s) from a thermophilic organism are used, the temperature may be chosen higher, for example up to 90° C.

Optimal temperature conditions can easily be identified for a specific enzyme by a person skilled in the art through routine experimentation based on common general knowledge and the information disclosed herein. For instance, for subtilisin, in particular subtilisin Carlsberg (e.g. in Alcalase®) the temperature may advantageously be in the range of 25-60° C. In case a combination of Alcalase® and Cal-B is used the temperature may advantageously be in the range 30-55° C.

The invention further relates to all possible combinations of different embodiments and/or preferred features according to the method according to the invention as described herein.

The invention will now be illustrated by the following examples.

EXAMPLES

Unless stated otherwise, chemicals were obtained from commercial sources and used without further purification. $^1$H NMR spectra were recorded on a Bruker Avance 300 MHz NMR (300.1 MHz) spectrometer; chemical shifts are given in ppm (δ) relative to $CDCl_3$ (7.26 ppm) unless stated otherwise.

Thin layer chromatography (TLC) was performed on pre-coated silica gel 60 $F_{254}$ plates (Merck); spots were visualized using UV light or ninhydrin.

3 Å molsieves (8 to 12 mesh, Acros) were activated under reduced pressure at 200° C. and t-butanol ($^t$BuOH) was stored on these molsieves. $^t$BuOH was pre-heated to a liquid (45° C.) before use.

Column chromatography was carried out using silica gel, Merck grade 9385 60 Å. Analytical HPLC was performed on an HP1090 Liquid Chromatograph, using a reversed-phase column (Inertsil ODS-3, C18, 5 µm, 150×4.6 mm) at 40° C. UV detection was performed at 220 nm using a UV-VIS 204 Linear spectrometer. The gradient program was: 0-25 min linear gradient ramp from 5% to 98% eluent B and from 25.1-30 min with 5% eluent B (eluent A: 0.5 mL/L methane sulfonic acid (MSA) in $H_2O$, eluent B 0.5 mL/L MSA in acetonitrile). The flow was 1 mL/min from 0-25.1 min and 2 mL/min from 25.2-29.8 min, then back to 1 mL/min until stop at 30 min. Injection volumes were 20 µL.

Alcalase-CLEA was purchased from CLEA-Technologies and contained 3.5 wt % water; the activity was 650 AGE units per gram (with 1 AGE unit catalyzing the formation of 1 µmol N-acetyl-glycine from N-acetyl-glycine ethyl ester at 40° C. and pH 7.5). This Alcalase-CLEA was treated as follows before use: 1 g Alcalase-CLEA was suspended in 20 mL $^t$BuOH and crushed with a spatula. After filtration, this procedure was repeated with 20 mL MTBE.

Cal-B (Novozymes, lipase Novozym-435 from *Candida Antarctica*, batch n. LC200204) was used without any pre-treatment.

Dipeptide reference compounds were chemically synthesized as follows: 1.0 mmol of amino acid amide HCl salt or amino acid $^t$Bu-ester HCl salt was dissolved in a mixture of 10 mL $CHCl_3$ and 30 mL EtOAc containing 355 µL diisopropylethylamine (DIPEA, 2.1 mmol, 2.1 eq). This solution was added to a solution (0° C.) of 1 mmol N-Cbz-protected amino acid (1 eq), 207 mg N-(3-dimethylaminopropyl)-N'-ethylcarbodiimide.HCl (EDCI.HCl, 1.1 mmol, 1.1 eq) and 150 mg 7-aza-N-hydroxybenzatriazole (HOAt, 1.2 mmol, 1.2 eq) in 20 mL $CHCl_3$. The mixture was stirred at ambient temperature for 16 h. The solution was concentrated in vacuo, the residue redissolved in 25 mL EtOAc, washed with 20 mL aqueous HCl (pH=3, 3×), 20 mL brine, 20 mL saturated aqueous $NaHCO_3$ (3×), 20 mL brine, dried ($Na_2SO_4$), and concentrated in vacuo. When needed, additional column chromatography using EtOAc/n-heptane mixtures was performed yielding the pure dipeptide.

N-Cbz-protected amino acid methyl esters were synthesized as follows: 100 mL MeOH was cooled to −80° C. with a bath of dry-ice in acetone followed by dropwise addition of 4 mL $SOCl_2$ (5.5 mmol, 3.7 eq). Subsequently, 1.5 mmol of the Cbz-protected amino acid was added and after removal of the bath the mixture was stirred at ambient temperature for 5 h. Volatiles were evaporated in vacuo and the remaining volatiles of the residue co-evaporated with MeOH (3×). The resulting residue was dried overnight in vacuo at ambient temperature yielding the pure N-Cbz-protected amino acid methyl ester.

Chemical synthesis of N-Cbz-protected amino acid carbamoylmethyl (Cam) or trifluoroethyl (Tfe) esters was performed as follows: 1 mmol of the N-Cbz-protected amino acid was dissolved in a mixture of 30 mL EtOAc and 5 mmol of carbamoylmethanol (CamOH) or 2,2,2-trifluoroethanol (TfeOH) (5 eq). Subsequently, 207 mg EDCI.HCl (1.1 mmol, 1.1 eq), 150 mg HOAt (1.2 mmol, 1.2 eq), 292 µL triethylamine (TEA, 1.1 mmol, 1.1 eq) were added. The reaction mixture was stirred at ambient temperature for 20 h. Subsequently, 20 mL EtOAc was added and the organic mixture was washed with 50 mL aqueous HCl (pH=3, 2×), 50 mL deionised water (2×), 50 mL brine, dried ($Na_2SO_4$), concentrated in vacuo and co-evaporated with 10 mL toluene (2×). When needed, additional column chromatography using EtOAc/n-heptane mixtures was performed yielding the pure ester.

| | $^1$H NMR and HPLC data for chemically synthesized starting materials and reference compounds | |
|---|---|---|
| | $^1$H NMR (CDCl$_3$) δ = | HPLC ret. time (min) |
| Starting material | | |
| Cbz-Ala-OMe | 1.35 (d, J = 6.6 Hz, 3 H), 3.68 (s, 3 H), 4.26-4.38 (m, 1 H), 5.04 (s, 2 H), 5.23 (d, J = 8.4 Hz, 1 H), 7.18-7.30 (m, 5 H) | 15.20 |
| Cbz-Ala-OCam | 1.40 (d, J = 6.0 Hz, 3 H), 4.23-4.29 (m, 1 H), 4.57 (dd, J = 15.0 and 23.4 Hz, 2 H), 5.05 (s, 2 H), 5.18 (d, J = 6.6 Hz, 1 H), 5.39 (s, 1 H), 6.65 (s, 1 H), 7.20-7.32 (m, 5 H) | 11.90 |
| Cbz-Ala-OTfe | 1.38 (d, J = 7.2 Hz, 3 H), 4.32-4.58 (m, 3 H), 5.05 (s, 2 H), 5.16 (d, J = 5.4 Hz, 1 H), 7.19-7.30 (m, 5 H) | 21.20 |
| Cbz-Phe-OMe | 3.09-3.14 (2xdd, 2 H), 3.72 (s, 3 H), 4.67 (dd, J = 3.0 and 10.5 Hz, 1 H), 5.10 (s, 2 H), 5.25 (d, J = 7.5 Hz, 1 H), 7.10 (dd, J = 1.5 and 10.2 Hz, 2 H), 7.26-7.34 (m, 8 H) | 19.09 |
| Cbz-Phe-OCam | 3.09 (d, J = 7.2 Hz, 2 H), 4.50-4.55 (m, 3 H), 5.06 (s, 2 H), 5.20 (d, J = 8.1 Hz, 1 H), 5.30 (s, 1 H), 6.33 (s, 1 H), 7.09 (dd, J = 1.5 and 8.1 Hz, 2 H), 7.23-7.32 (m, 8 H) | 15.30 |
| Cbz-Phe-OTfe | 2.99-3.10 (2xdd, 2 H), 4.37-4.46 (m, 2 H), 4.68 (dd, J = 6.3 and 14.1 Hz, 1 H), 5.02 (s, 2 H), 5.08 (d, J = 8.1 Hz, 1 H), 7.05 (dd, J = 1.5 and 7.2 Hz, 2H), 7.19-7.28 (m, 8 H) | 23.36 |
| Cbz-Val-OMe | 0.85 (2xd, 6 H), 2.06-2.12 (m, 1 H), 3.67 (s, 3 H), 4.23 (dd, J = 4.8 and 9.0 Hz, 1 H), 5.04 (s, 2 H), 5.19 (d, J = 8.1 Hz, 1 H), 7.19-7.29 (m, 5 H) | 17.96 |
| Cbz-Val-OCam | 0.89 (dd, J = 6.9 and 6.9 Hz, 6 H), 2.03-2.10 (m, 1 H), 4.12 (dd, J = 6.3 and 6.3 Hz, 1 H), 4.48 (dd, J = 15.0 and 57.0 Hz, 2 H), 5.01 (s, 2 H), 5.71 (d, J = 7.5 Hz, 1 H), 6.26 (s, 1 H), 6.71 (s, 1 H), 7.19-7.25 (m, 5 H) | 14.31 |
| Cbz-D-Ala-OMe | 1.33 (d, J = 7.2 Hz, 3 H), 3.66 (s, 3 H), 4.29-4.34 (m, 1 H), 5.03 (s, 2 H), 5.24 (d, J = 9.3 Hz, 1 H), 7.18-7.28 (m, 5 H) | 15.18 |
| Cbz-D-Ala-OCam | 1.41 (d, J = 7.2 Hz, 3 H), 4.23-4.28 (m, 1 H), 4.56 (dd, J = 15.6 and 24.0 Hz, 2 H), 5.04 (s, 2 H), 5.16 (d, J = 6.3 Hz, 1 H), 5.39 (s, 1 H), 6.63 (s, 1 H), 7.19-7.30 (m, 5 H) | 11.91 |
| Cbz-D-Phe-OMe | 3.09-3.14 (2xdd, 2 H), 3.72 (s, 3 H), 4.68 (dd, J = 3.3 and 11.1 Hz 1 H), 5.10 (s, 2 H), 5.22 (d, J = 7.5 Hz, 1 H), 7.09 (dd, J = 1.8 and 7.2 Hz, 2 H), 7.25-7.37 (m, 8 H) | 19.13 |
| Cbz-D-Phe-OCam | 3.05 (d, J = 7.2 Hz, 2 H), 4.35-4.50 (m, 3 H), 5.01 (s, 2 H), 5.20 (d, J = 9.0 Hz, 1 H), 5.32 (s, 1 H), 6.29 (s, 1 H), 7.09 (dd, J = 1.5 and 8.1 Hz, 2 H), 7.19-7.27 (m, 8 H) | 15.32 |
| Reference compound | | |
| Cbz-Ala-Leu-NH$_2$ | 0.85 (2xd, J = 6.6 and 6.6 Hz, 6 H), 1.32 (d, J = 7.2 Hz, 3 H), 1.52-1.73 (m, 3 H), 4.13 (m, 1 H), 4.37 (m, 1 H), 5.04 (s, 2 H), 5.23 (d, J = 4.5 Hz, 1 H), 5.25 (s, 1 H), 6.20 (s, 1 H), 6.32 (d, J = 7.8 Hz, 1 H), 7.19-7.29 (m, 5 H) | 13.80 |
| Cbz-Ala-Pro-NH$_2$ | 1.29 (d, J = 6.6 Hz, 3 H), 1.73-2.31 (m, 4 H), 3.49-3.61 (m, 2 H), 4.45-4.54 (m, 2 H), 5.02 (s, 2 H), 5.39 (s, 1H), 5.57 (d, J = 7.5 Hz, 1 H), 6.65 (s, 1 H), 7.19-7.29 (m, 5 H) | 11.30 |
| Cbz-Phe-Leu-NH$_2$ | 0.73 (d, J = 6.0 Hz, 6 H), 1.06-1.35 (m, 3 H), 3.00 (dd, J = 6.3 and 6.3 Hz, 2 H), 4.19-4.27 (2xdd, 2 H), 5.00 (s, 2 H), 5.13 (s, 1 H), 5.25 (d, J = 5.1 Hz, 1 H), 5.88 (d, J = 7.2 Hz, 1 H), 6.34 (s, 1 H) 7.09 (dd, 2 H), 7.17-7.31 (m, 8 H) | 17.00 |
| Cbz-Phe-Leu-O$^t$Bu | 0.80 (d, J = 6.0 Hz, 6 H), 1.36-1.50 (m, 12 H), 3.00 (d, J = 6.3 Hz, 2 H), 4.32-4.39 (2xdd, 2 H), 5.00 (s, 2 H), 5.29 (d, J = 5.4 Hz, 1 H), 6.23 (d, J = 6.9 Hz, 1 H), 7.09-7.25 (m, 10 H) | 23.02 |
| Cbz-Phe-Pro-NH$_2$ | 1.57-1.82 (m, 4 H), 2.92-3.02 (dd, 2 H), 3.40-3.57 (2xdd, 2 H), 4.47 (dd, J = 1.5 and 6.9 Hz, 1 H), 4.67 (dd, J = 7.2 and 15.0 Hz, 1 H), 5.02 (s, 2 H), 5.49 (s, 1 H), 5.73 (d, J = 8.4 Hz, 1 H), 6.35 (s, 1 H), 7.15-7.27 (m, 10 H) | 14.56 |
| Cbz-Phe-Pro-O$^t$Bu | 1.41 (s, 9 H), 1.58-2.08 (m, 4 H), 2.82 (dd, J = 6.0 and 14.1 Hz, 1 H), 3.08 (dd, J = 6.0 and 14.1 | 14.72 |

¹H NMR and HPLC data for chemically synthesized starting materials and reference compounds

| | ¹H NMR (CDCl₃) δ = | HPLC ret. time (min) |
|---|---|---|
| | Hz, 1 H), 3.22-3.61 (2xdd, 2 H), 4.32 (dd, 1 H), 4.63 (dd, 1 H), 4.96 (s, 2 H), 5.45 (d, J = 11.7 Hz, 1 H), 7.18-7.26 (m, 10 H) | |
| Cbz-Val-Leu-NH₂ | (note: measured in DMSO-d6) 0.81-0.88 (m, 12 H), 1.41-1.60 (m, 3 H), 1.94-2.01 (m, 1 H), 3.84 (m, 1 H), 4.25 (m, 1 H), 5.03 (s, 2 H), 6.95 (s, 1 H), 7.29-7.36 (m, 7 H), 7.86 (d, J = 8.4 Hz, 1 H) | 15.47 |
| Cbz-Val-Pro-NH₂ | 0.90 (2xd, 6 H), 1.73-2.17 (m, 4 H), 2.24-2.30 (m, 1 H), 3.50-3.70 (2xdd, 2 H), 4.27 (dd, J = 6.9 and 9.0 Hz, 1 H), 4.51 (dd, J = 2.7 and 7.8 Hz, 1 H), 5.01 (s, 2 H), 5.44 (s, 1 H), 5.50 (d, J = 9.0 Hz, 1 H), 6.74 (s, 1 H), 7.19-7.29 (m, 5 H) | 13.34 |
| Cbz-D-Ala-Leu-NH₂ | 0.83 (2xd, J = 6.6 and 6.6 Hz, 6 H), 1.31 (d, J = 7.2 Hz, 3 H), 1.52-1.69 (m, 3 H), 4.13 (m, 1 H), 4.34 (m, 1 H), 5.02 (s, 2 H), 5.23 (d, J = 4.5 Hz, 1 H), 5.26 (s, 1 H), 6.21 (s, 1 H), 6.30 (d, J = 7.5 Hz, 1 H), 7.18-7.30 (m, 5 H) | 13.76 |
| Cbz-D-Ala-Pro-NH₂ | 1.30 (d, J = 6.9 Hz, 3 H), 1.72-2.30 (m, 4 H), 3.49-3.60 (m, 2 H), 4.46-4.54 (m, 2 H), 5.04 (s, 2 H), 5.40 (s, 1H), 5.56 (d, J = 7.5 Hz, 1 H), 6.67 (s, 1 H), 7.17-7.28 (m, 5 H) | 11.28 |
| Cbz-D-Phe-Leu-NH₂ | 0.74 (d, J = 6.0 Hz, 6 H), 1.09-1.33 (m, 3 H), 3.02 (dd, J = 6.3 and 6.3 Hz, 2 H), 4.21-4.28 (2xdd, 2 H), 5.03 (s, 2 H), 5.10 (s, 1 H), 5.28 (d, J = 5.1 Hz, 1 H), 5.89 (d, J = 6.9 Hz, 1 H), 6.36 (s, 1 H), 7.10 (dd, 2 H), 7.17-7.33 (m, 10 H) | 17.04 |
| Cbz-D-Phe-Pro-NH₂ | 1.56-1.83 (m, 4 H), 2.90-3.01 (dd, 2 H), 3.40-3.56 (2xdd, 2 H), 4.46 (dd, J = 1.8 and 7.5 Hz, 1 H), 4.65 (dd, J = 7.5 and 15.6 Hz, 1 H), 5.03 (s, 2 H), 5.50 (s, 1 H), 5.70 (d, J = 8.4 Hz, 1 H), 6.34 (s, 1 H), 7.18-7.29 (m, 10 H) | 14.60 |

Example 1

Enzymatic Synthesis of Dipeptides Starting from Me, Cam and Tfe Esters a Using Alcalase-CLEA

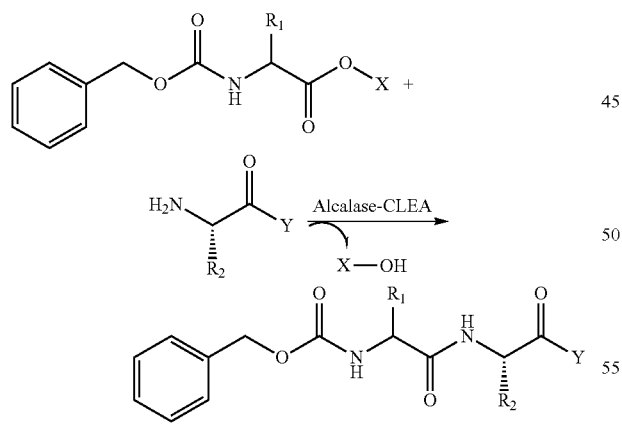

$R_1$ and $R_2$ = Amino acid side chains
$X = CH_3$, $CH_2C(O)NH_2$ or $CH_2CF_3$
$Y = O^tBu$ or $NH_2$ 300 mg Alcalase-CLEA was added to a mixture of 3 mL MTBE and 200 mg 3 Å molsieves. Subsequently, 100 mg N-Cbz-protected amino acid ester and 1.0 equiv. of C-terminal protected amino acid were added. The mixture was shaken at 50° C. at 150 rpm for 16 h. After filtration, the solids were washed with 10 mL EtOAc (3×). The combined organic layers were washed with 25 mL saturated aqueous NaHCO₃ solution (3×), 25 mL aqueous HCl solution (pH=3, 3×), 25 mL brine, dried (Na₂SO₄), concentrated in vacuo, and co-evaporated with 20 mL toluene (2×) and 20 mL CHCl₃ (2×). When needed, additional column chromatography using EtOAc/n-heptane mixtures was performed yielding the pure dipeptide. The HPLC retention times and ¹H NMR spectra of all obtained dipeptides fully corresponded to those of the reference compounds. The obtained yields are given in the table below.

| Product | From (ester) | Purified yield (%) |
|---|---|---|
| Cbz-Phe-Leu-O$^t$Bu | Me | 61 |
| Cbz-Phe-Leu-O$^t$Bu | Cam | 87 |
| Cbz-Phe-Pro-O$^t$Bu | Me | 37 |
| Cbz-Phe-Pro-O$^t$Bu | Cam | 92 |
| Cbz-Phe-Pro-NH₂ | Me | 27 |
| Cbz-Phe-Pro-NH₂ | Cam | 91 |
| Cbz-Phe-Pro-NH₂ | Tfe | 93 |
| Cbz-Phe-Leu-NH₂ | Me | 89 |
| Cbz-Phe-Leu-NH₂ | Cam | 91 |
| Cbz-Phe-Leu-NH₂ | Tfe | 90 |
| Cbz-Val-Leu-NH₂ | Me | 13 |
| Cbz-Val-Leu-NH₂ | Cam | 93 |
| Cbz-Val-Pro-NH₂ | Me | 17 |
| Cbz-Val-Pro-NH₂ | Cam | 76 |
| Cbz-D-Ala-Leu-NH₂ | Me | 87 |
| Cbz-D-Ala-Leu-NH₂ | Cam | 92 |
| Cbz-D-Ala-Pro-NH₂ | Me | 9 |
| Cbz-D-Ala-Pro-NH₂ | Cam | 69 |
| Cbz-D-Phe-Leu-NH₂ | Me | 61 |
| Cbz-D-Phe-Leu-NH₂ | Cam | 93 |
| Cbz-D-Phe-Pro-NH₂ | Me | 0 |
| Cbz-D-Phe-Pro-NH₂ | Cam | 50 |

| Product | From (ester) | Purified yield (%) |
| --- | --- | --- |
| Cbz-Ala-Leu-NH$_2$ | Tfe | 94 |
| Cbz-Ala-Pro-NH$_2$ | Tfe | 90 |

Example 2

Enzymatic Synthesis of Cam and Tfe Esters

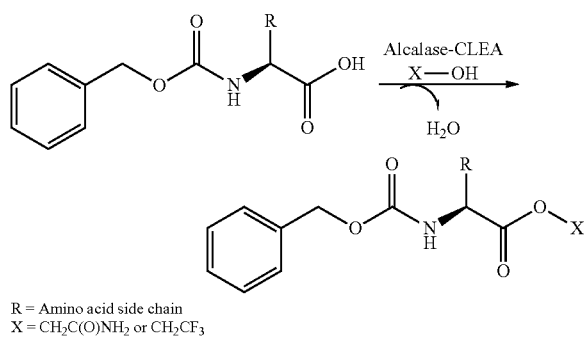

R = Amino acid side chain
X = CH$_2$C(O)NH$_2$ or CH$_2$CF$_3$

Several Cam and Tfe esters were synthesized using one of the protocols 1, 2 or 3, as indicated below.

Protocol 1: Synthesis of Cam or Tfe Esters Using Alcalase-CLEA 300 mg Alcalase-CLEA was added to a mixture of 3 mL MTBE, 200 mg 3 Å molsieves, 200 mg of carbamoylmethanol or 2,2,2-trifluoroethanol and 50 mg N-Cbz-protected amino acid. The mixture was shaken at 50° C. at 150 rpm for 72 h. After filtration, the solids were washed with 10 mL EtOAc (3×). The combined organic layers were washed with 25 mL deionised water (3×), 25 mL aqueous HCl solution (pH=3, 3 x), 25 mL brine, dried (Na$_2$SO$_4$), concentrated in vacuo, and co-evaporated with 20 mL toluene (2×) and 20 mL CHCl$_3$ (2×).

Protocol 2: Synthesis of Cam or Tfe Esters Using Cal-B 100 mg Cal-B was added to a mixture of 3 mL acetonitrile, 100 mg 3 Å molsieves, 200 mg of carbamoylmethanol or 2,2,2-trifluoroethanol and 50 mg N-Cbz-protected amino acid. The mixture was shaken at 50° C. at 150 rpm for 16 h. After filtration, the solids were washed with 10 mL EtOAc (3×). The combined organic layers were washed with 25 mL deionised water (3×), 25 mL aqueous HCl solution (pH=3, 3 x), 25 mL brine, dried (Na$_2$SO$_4$), concentrated in vacuo, and co-evaporated with 20 mL toluene (2×) and 20 mL CHCl$_3$ (2×). When needed, additional column chromatography using EtOAc/n-heptane mixtures was performed yielding the pure ester.

| Product | Protocol | Enzyme | Purified yield (%) |
| --- | --- | --- | --- |
| Cbz-Phe-OCam | 1 | Alcalase-CLEA | 24 |
| Cbz-Phe-OTfe | 1 | Alcalase-CLEA | 57 |
| Cbz-Ala-OCam | 1 | Alcalase-CLEA | 21 |
| Cbz-Ala-OTfe | 1 | Alcalase-CLEA | 55 |
| Cbz-Ala-OTfe | 2 | Cal-B | 77 |
| Cbz-Ala-OCam | 2 | Cal-B | 65 |

Protocol 3: Synthesis of Tfe Esters Using Cal-B 100 mg Cal-B was added to a mixture of 3 mL MBTE, 100 mg 3 Å molsieves, 200 mg 2,2,2-trifluoroethanol and 50 mg N-Cbz-protected amino acid. The mixture was shaken at 50° C. at 150 rpm for 54 h. The conversion to the corresponding Tfe ester was determined by HPLC analysis.

| Product | HPLC yield (%) |
| --- | --- |
| Cbz-Ala-OTfe | 98 |
| Cbz-D-Ala-OTfe | 62 |
| Cbz-Gly-OTfe | 87 |
| Cbz-Met-OTfe | 88 |
| Cbz-Pro-OTfe | 92 |

Example 3

Enzymatic Synthesis of Dipeptides Using Cam or Tfe Alcohol as Additive

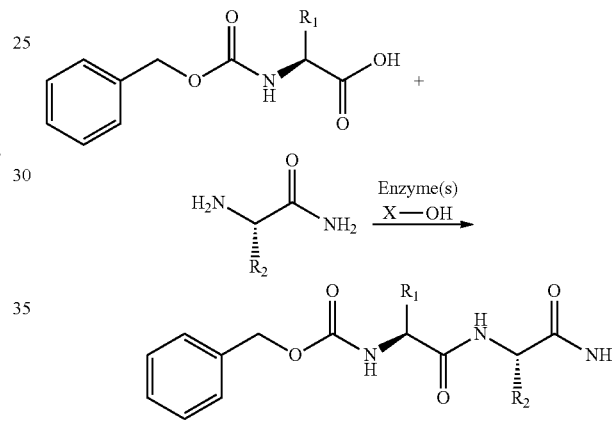

R$_1$ and R$_2$ = Amino acid side chains
X = CH$_2$C(O)NH$_2$ or CH$_2$CF$_3$

Several dipeptides were synthesized using one of the protocols 1-3 as indicated below.

Protocol 1: Synthesis of Dipeptides Using Cam or Tfe Alcohol as Additive with Alcalase-CLEA.

300 mg Alcalase-CLEA was added to a mixture of 3 mL MTBE, 200 mg 3 Å molsieves and 200 mg of the appropriate alcohol. Subsequently, 50 mg N-Cbz-protected amino acid and 1 equiv. of amino acid amide were added. The mixture was shaken at 50° C. with 150 rpm for 16 h.

Protocol 2: Synthesis of dipeptides using Cam or Tfe alcohol as additive with Cal-B.

100 mg Cal-B was added to a mixture of 3 mL acetonitrile, 200 mg 3 Å molsieves and 200 mg of the appropriate alcohol. Subsequently, 50 mg N-Cbz-protected amino acid and 1 equiv. of amino acid amide were added. The mixture was shaken at 50° C. with 150 rpm for 16 h.

Protocol 3: Synthesis of dipeptides using Cam or Tfe alcohol as additives with Alcalase-CLEA and Cal-B.

300 mg Alcalase-CLEA and 100 mg Cal-B were added to a mixture of 3 mL acetonitril, 200 mg 3 Å molsieves and 200 mg of the appropriate alcohol. Subsequently, 50 mg N-Cbz-protected amino acid and 1 equiv. of amino acid amide were added. The mixture was shaken at 50° C. with 150 rpm for 16 h. After filtration, the enzyme was washed with 10 mL EtOAc (3×). The combined organic layers were washed with 25 mL deionised water (3×), 25 mL aqueous HCl solution (pH=3, 3×), 25 mL brine, dried (Na$_2$SO$_4$), concentrated in vacuo, and co-evaporated with 20 mL toluene (2×) and 20 mL CHCl$_3$ (2×).

Example 4

Enzymatic Synthesis of Tfe Esters of Di- and Tripeptides Using Cal-B 100 mg Cal-B was added to a mixture of 3 mL methyl tert-butyl ether, 100 mg 3 Å molsieves, 200 mg 2,2,2-trifluoroethanol and 50 mg N-Cbz-protected di- or tripeptide. The mixture was shaken at 50° C. and 150 rpm. The conversion to the corresponding C-terminal Tfe ester was monitored by HPLC analysis. In all cases the starting compound was converted to only the corresponding C-terminal Tfe ester. The HPLC retention times of the starting compounds and the Tfe ester products (P) are shown in the table below.

| Starting compound | Retention time starting compound | Tfe ester product (P) | Retention time P |
|---|---|---|---|
| Cbz-Ala-Ala | 10.38 min | Cbz-Ala-Ala-OTfe | 17.35 min |
| Cbz-Val-Val-Pro | 13.37 min | Cbz-Val-Val-Pro-OTfe | 19.14 min |
| Cbz-Val-Pro-Pro | 11.45 min | Cbz-Val-Pro-Pro-OTfe | 17.75 min |
| Cbz-Pro-Leu-Gly | 13.68 min | Cbz-Pro-Leu-Gly-OTfe | 19.47 min |
| Cbz-Gly-Phe-Ala | 13.58 min | Cbz-Gly-Phe-Ala-OTfe | 19.17 min |
| Cbz-Gly-Ile-Ala | 12.33 min | Cbz-Gly-Ile-Ala-OTfe | 18.53 min |
| Cbz-Gly-Leu-Ala | 11.21 min | Cbz-Gly-Leu-Ala-OTfe | 17.96 min |

Samples were taken from the reaction mixtures after 1 and/or 2 and/or 3 and/or 7 days. The % Tfe ester product (% P) values, as shown in the table below, were calculated by the formula:

% $P$=area % Tfe ester product/(area % starting compound+area % Tfe ester product).

| Starting compound | Tfe ester product (P) | % P after 1 day | % P after 2 days | % P after 3 days | % P after 7 days |
|---|---|---|---|---|---|
| Cbz-Ala-Ala | Cbz-Ala-Ala-OTfe | 85% | n.d. | 86% | 97% |
| Cbz-Val-Val-Pro | Cbz-Val-Val-Pro-OTfe | n.d. | 35% | n.d. | 50% |
| Cbz-Val-Pro-Pro | Cbz-Val-Pro-Pro-OTfe | n.d. | 74% | n.d. | n.d. |
| Cbz-Pro-Leu-Gly | Cbz-Pro-Leu-Gly-OTfe | 5% | n.d. | 21% | 49% |
| Cbz-Gly-Phe-Ala | Cbz-Gly-Phe-Ala-OTfe | 97% | n.d. | 97% | n.d. |
| Cbz-Gly-Ile-Ala | Cbz-Gly-Ile-Ala-OTfe | 48% | n.d. | 91% | n.d. |
| Cbz-Gly-Leu-Ala | Cbz-Gly-Leu-Ala-OTfe | 51% | 58% | n.d. | 85% |

[n.d. = not determined]

The reaction mixture of the esterification of Cbz-Ala-Ala to Cbz-Ala-Ala-OTfe was worked up as follows. The reaction mixture obtained after 7 days was filtrated and the solids were washed with 10 mL EtOAc (3×). The combined organic layers were washed with 25 mL deionized water (3×), 25 mL aqueous HCl solution (pH=3, 3×), 25 mL brine, dried (Na$_2$SO$_4$) and concentrated in vacuo. The volatiles in the resulting residue were removed by coevaporation with 20 mL toluene (2×) and with 20 mL CHCl$_3$ (2×). Chromatographic purification of the product gave pure Cbz-Ala-Ala-OTfe in 85% yield.

$^1$H NMR (300 MHz, CDCl$_3$) δ=1.32 (d, J=7.4 Hz, 3 H, CH$_3$), 1.37 (d, J=7.3 Hz, 3 H, CH$_3$), 4.13-4.24 (m, 1 H, C$_\alpha$H), 4.29-4.40 (m, 1 H, C$_\alpha$H), 4.49-4.61 (m, 2 H, OCH$_2$CF$_3$), 5.05 (s, 2 H, CH$_2$OCO), 5.18 (bs, 1 H, NH), 6.41 (bs, 1 H, NH), 7.28 (m, 5 H, C$_{Ar}$H);

$^{13}$C NMR (75 MHz, CDCl$_3$) δ=16.7, 16.8, 46.9, 49.4, 60.0, 66.1, 119.8, 123.5, 127.1, 127.3, 127.6, 138.3, 170.2, 170.9.

| Product | Enzyme(s) | Protocol | Alcohol | Yield (%) |
|---|---|---|---|---|
| Cbz-Ala-Leu-NH$_2$ | Alcalase-CLEA | 1 | Tfe-OH | 13 |
| Cbz-Ala-Leu-NH$_2$ | Cal-B | 2 | Tfe-OH | 31 |
| Cbz-Ala-Leu-NH$_2$ | Cal-B and Alcalase-CLEA | 3 | Tfe-OH | 87 |
| Cbz-Ala-Pro-NH$_2$ | Alcalase-CLEA | 1 | Tfe-OH | 9 |
| Cbz-Ala-Pro-NH$_2$ | Cal-B | 2 | Tfe-OH | 14 |
| Cbz-Ala-Pro-NH$_2$ | Cal-B and Alcalase-CLEA | 3 | Tfe-OH | 27 |
| Cbz-Ala-Leu-NH$_2$ | Alcalase-CLEA | 1 | Cam-OH | 15 |
| Cbz-Ala-Leu-NH$_2$ | Cal-B and Alcalase-CLEA | 3 | Cam-OH | 88 |
| Cbz-Ala-Pro-NH$_2$ | Alcalase-CLEA | 1 | Cam-OH | 11 |
| Cbz-Ala-Pro-NH$_2$ | Cal-B and Alcalase-CLEA | 3 | Cam-OH | 31 |

The invention claimed is:

1. A method for enzymatically synthesising a peptide, comprising enzymatically preparing an ester or a thioester from
   (i) an N-terminal protected amino acid, an N-terminal protected amino acid C-terminal ester, an N-terminal protected peptide, or an N-terminal protected peptide C-terminal ester and
   (ii) an alcohol represented by the formula HO—CX$_2$—Z or a thiol represented by the formula HS—CX$_2$—Z, each X independently representing a halogen atom or a hydrogen atom; and Z represents an electron withdrawing group comprising at least one sp$^3$-hybridised carbon comprising at least two substituents comprising a heteroatom directly attached to the at least one sp$^3$-hybridised carbon or at least one sp$^2$-hybridised carbon comprising one or two substituents comprising a heteroatom directly attached to the at least one sp$^2$-hybridised carbon,
   the preparation of the ester or thioester being carried out in a reaction medium comprising 2 wt. % water or less based on the weight of liquids in the reaction medium; and
   enzymatically coupling the prepared ester or thioester with an optionally C-terminal protected amino acid or with an optionally C-terminal protected peptide, in a reaction medium comprising 2 wt. % water or less based on the total weight of the reaction medium, thereby synthesising the peptide.

2. The method according to claim 1, wherein the coupling is carried out with the enzyme used for catalysing the preparation of the ester or thioester.

3. The method according to claim 1, wherein the preparation of the ester or thioester and the coupling are each catalysed by at least one enzyme selected from the group of lipases, esterases and proteases.

4. The method according to claim 3, wherein
a) a protease catalyzes the preparation of the ester or thioester and a lipase or esterase catalyze the coupling reaction;
b) a lipase catalyzes the preparation of the ester or thioester and a protease or esterase catalyze the coupling reaction; or
c) an esterase catalyzes the preparation of the ester or thioester and a protease or lipase catalyze the coupling reaction.

5. The method according to claim 3, wherein both the preparation of the ester or thioester and the coupling are catalysed by a single enzyme selected from the group of lipases, esterases and proteases.

6. The method according to claim 3, wherein the lipase is selected from the group of lipases from *Candida*.

7. The method according to claim 6, wherein the *Candida* lipase is a *Candida antarctica* lipase.

8. The method according to claim 7, wherein the *Candida antarctica* lipase is a *Candida antartica* lipase B.

9. The method according to claim 3, wherein the protease is selected from the group of serine-type carboxypeptidases, metal locarboxypeptidases, cysteine-type carboxypeptidases, serine endopeptidases, cysteine endopeptidases, aspartic endopeptidases and metalloendopeptidases.

10. The method according to claim 9, wherein the serine endopeptidases are subtilisins.

11. Method according to claim 10, wherein the subtilisin is subtilisin Carlsberg.

12. The method according to claim 1, wherein at least one enzyme is immobilised.

13. The method according to claim 1, wherein the preparation of the ester or thioester and the coupling are carried out in a reaction medium comprising 1.0 wt. % or less water.

14. The method according to claim 13, wherein the preparation of the ester or thioester and the coupling are carried out in a reaction medium comprising 0.5 wt. % or less water.

15. The method according to claim 14, wherein the preparation of the ester or thioester and the coupling are carried out in a reaction medium comprising 0.1 wt. % or less water.

16. The method according to claim 1, wherein Z is a carbamoyl group, a trifluoromethyl group or a trichloromethyl group.

17. The method according to claim 1, wherein both X's represent a hydrogen.

18. the method according to claim 1, wherein the preparation of the ester or thioester is carried out in the presence of the optionally C-terminal protected amino acid or optionally C-terminal protected peptide with which the ester or thioester that is prepared is to be coupled and in the presence of the enzyme catalysing the coupling reaction.

19. The method according to claim 1, wherein the optionally C-terminal protected amino acid or the optionally C-terminal protected peptide is added after the ester or thioester has been prepared.

20. The method according to claim 1, wherein the coupling is carried out without first isolating the prepared ester or thioester from the reaction medium.

21. The method according to claim 1, wherein Z is selected from the group of $-C(=O)R^1, -C(=S)R^1, -OR^2$ or $-SR^2$, wherein
$R^1$ is $NH_2$, $NHCH_3$, $N(CH_3)_2$, an alpha amino acid, a C-terminal protected alpha-amino acid, a peptide, a C-terminal protected peptide, $-OH$, or a salt thereof, alkyl or aryl groups wherein said alkyl or aryl groups comprises one or more halogen substituents, and
$R^2$ is hydrocarbon or substituted hydrocarbon having one or more halogen substituents.

* * * * *